United States Patent [19]

Jordon

[11] 4,265,230

[45] May 5, 1981

[54] TRACTION SPLINT

[76] Inventor: Donald A. Jordon, 3 Kenleigh Grove, Armadale, Victoria, Australia

[21] Appl. No.: 51,336

[22] Filed: Jun. 22, 1979

[30] Foreign Application Priority Data

Jul. 11, 1978 [AU] Australia .............................. PD5030

[51] Int. Cl.³ .............................................. A61F 5/04
[52] U.S. Cl. ................................ 128/87 R; 128/84 C
[58] Field of Search ...................... 128/84 R, 84 C, 85, 128/87 R

[56] References Cited

U.S. PATENT DOCUMENTS

| 959,389 | 5/1910 | Rodgers | 128/85 |
| 1,226,013 | 5/1917 | Roth | 128/85 X |
| 2,198,908 | 4/1940 | Ellis | 128/85 UX |
| 3,419,002 | 12/1968 | Santosus | 128/85 |
| 3,906,942 | 9/1975 | Lumb, Jr. et al. | 128/84 C |
| 4,174,709 | 11/1979 | Maddux | 128/85 |

Primary Examiner—John D. Yasko
Attorney, Agent, or Firm—Beveridge, DeGrandi, Kline and Lunsford

[57] ABSTRACT

To enable a traction splint to be applied to a patient's limb without substantial disturbance of the limb, the splint comprises a thrust member in the form of a collar-like strap sidewardly applicable to the injured limb where it joins the trunk of the body, a U-shaped caliper, to accept the injured limb, having its free ends locatable in relation to stubs projecting from the thrust member, and having a crotch end to which a tether secured to the distal end of the injured limb is selectively attachable so to vary the tensional load imposed on the limb.

7 Claims, 11 Drawing Figures

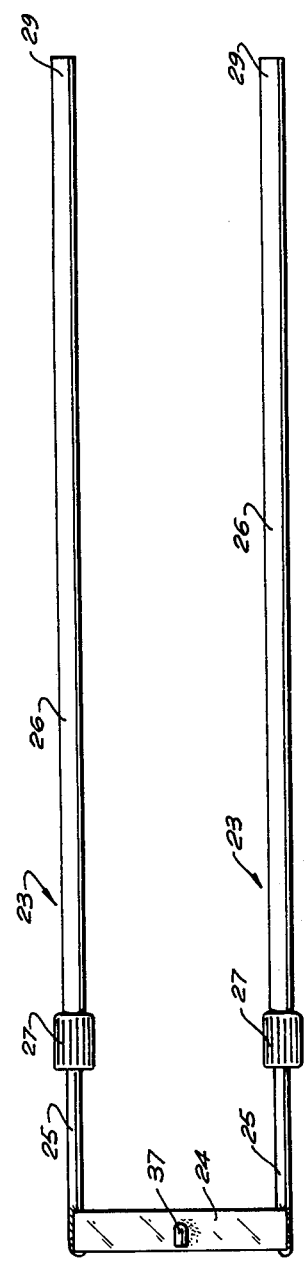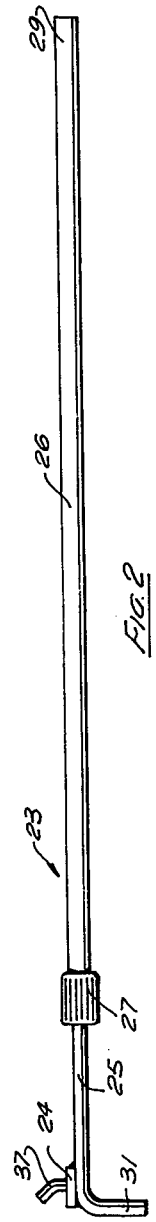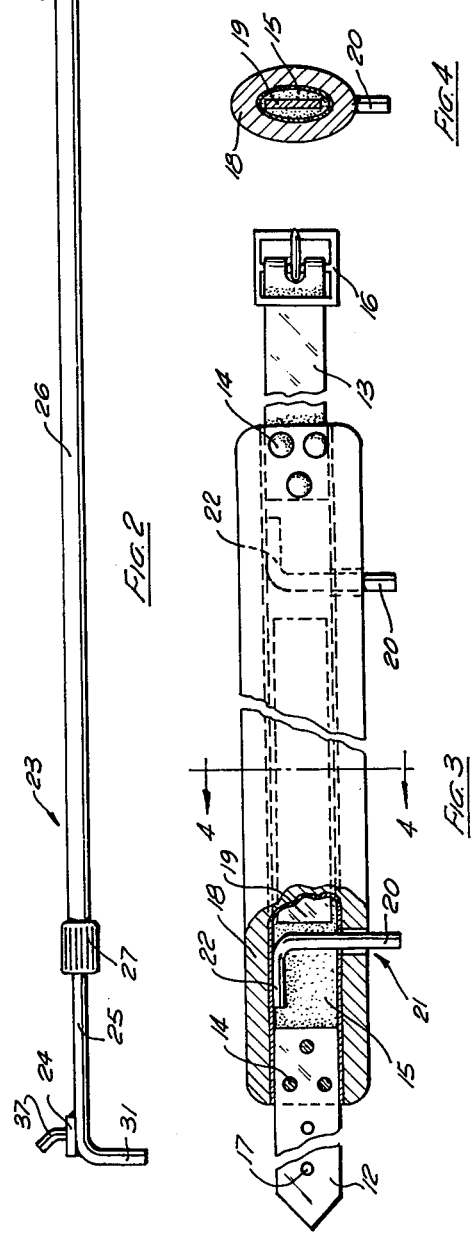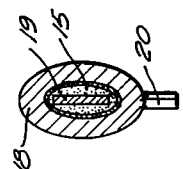

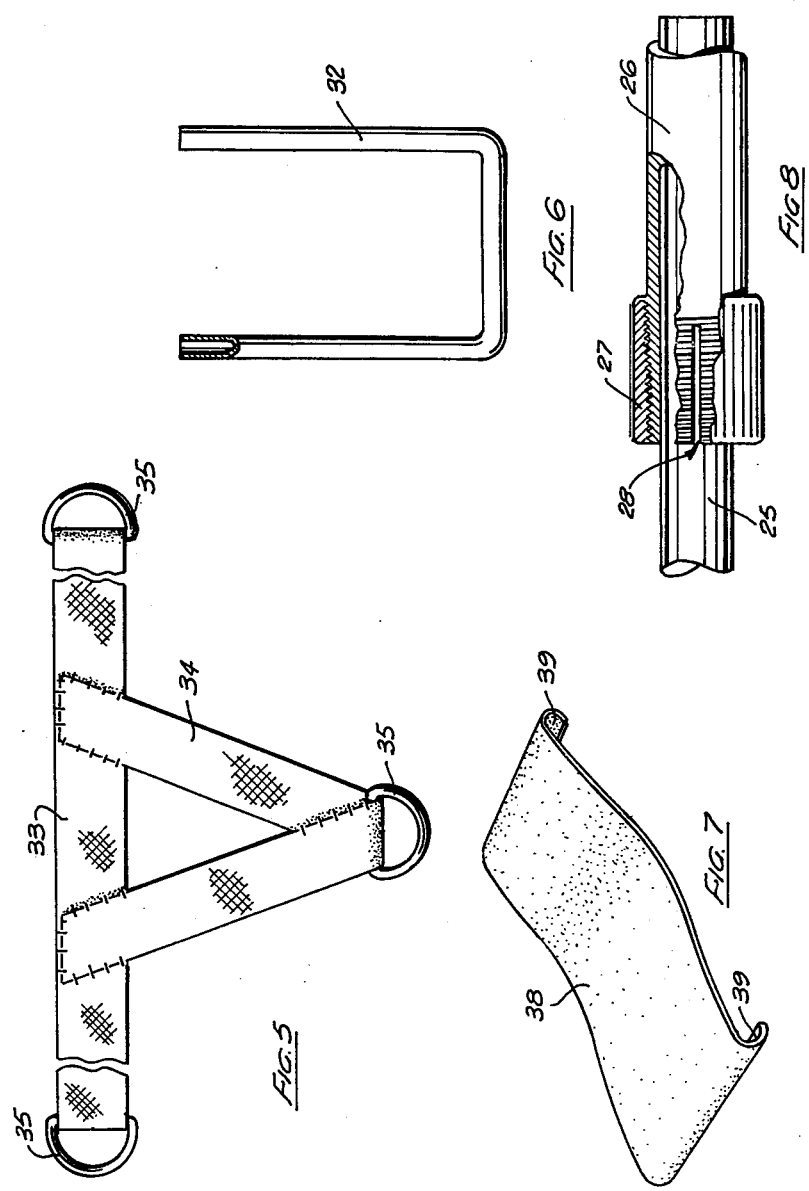

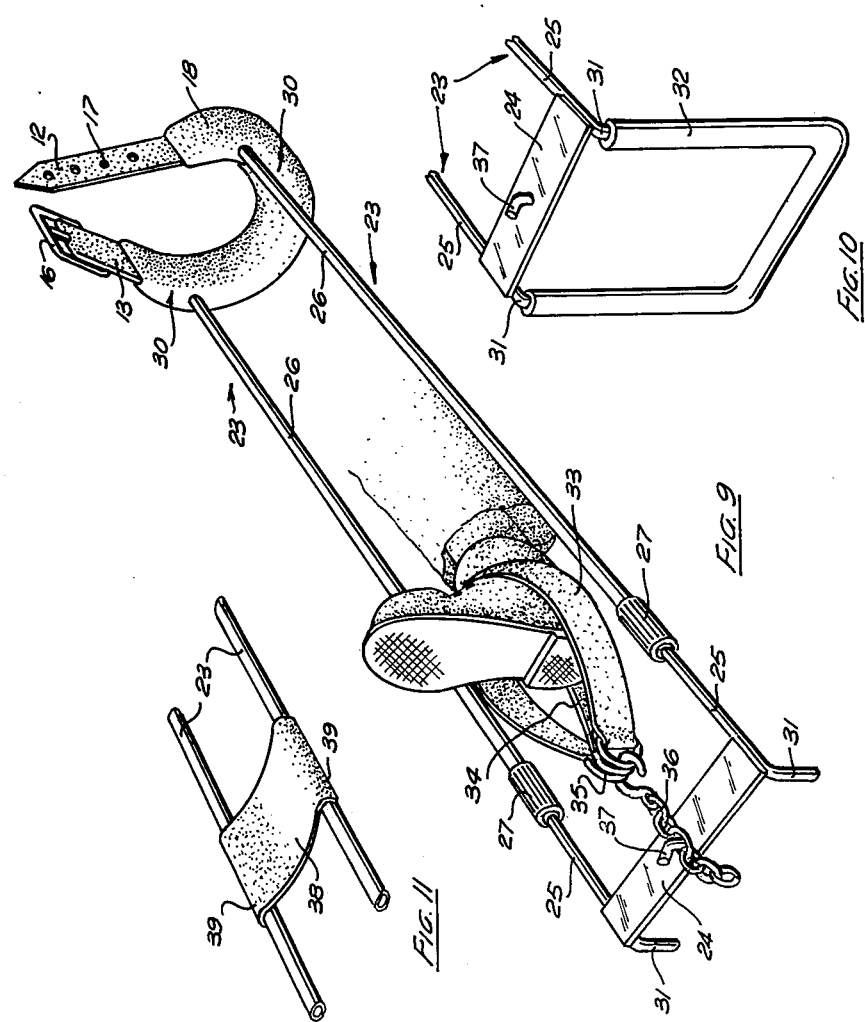

TRACTION SPLINT

This invention relates to traction splints; namely, those splints applicable to broken limbs to keep the fractured bone parts in required alignment and at the same time hold the broken limb in sufficient tension as will ease pain due to the fracture.

The object of the invention is to provide a traction splint which can be applied to a broken limb without having to lift the limb or otherwise cause its substantial disturbance, and which is of inexpensive, simple construction and particularly suited for on-site use under emergency conditions such as those, for example, due to a traffic accident.

The invention provides a traction splint comprising:

(a) a thrust member sidewardly applicable to the proximal end of a patient's limb, and, adapted, when so applied, to bear against the patient's trunk at that proximal end, (b) a U-shaped caliper including length adjustable side members able to flank a broken limb longitudinally and on either side thereof, with the caliper crotch spaced from the distal end of the patient's limb, (c) means to locate and retain location of the free ends of said side members in relation to said thrust member, and (d) tension means able to take hold of the distal end of a patient's limb which has said caliper and said thrust member applied thereto as aforesaid, and adapted for attachment to said caliper crotch thereby to exert a degree of tension on the patient's limb.

An example of the invention is illustrated in the drawings herewith.

FIG. 1 is a plan of the U-shaped caliper.

FIG. 2 is a side elevation projected from FIG. 1.

FIG. 3 is a partly sectioned side elevation of a thrust ring when laid out flat.

FIG. 4 is a sectional end elevation taken on line 4—4 in FIG. 3.

FIG. 5 is a side elevation of a strap element forming part of the mentioned tension means.

FIG. 6 is a side elevation of an elevator stand applicable to the crotch end of the caliper.

FIG. 7 is a perspective view of a supporting bridge-piece usable with the caliper.

FIG. 8 is a partly sectioned side elevation (on an enlarged scale) of a chuck for holding selected adjustment of a caliper side member.

FIG. 9 is a perspective view showing the main portions of the traction splint.

FIG. 10 shows the crotch end portion of the traction splint with an elevator of the kind shown in FIG. 6 applied thereto.

FIG. 11 is a perspective of two caliper side members partly broken away and a bridge piece of the kind shown in FIG. 7 applied thereto.

Referring to the illustrated embodiment, the thrust member is in the form of a strap having end portions 12 and 13 secured (by rivets 14) to the respective ends of a tubular body portion 15. Means are provided, such as buckle 16 and holes 17, to enable the strap member to be applied to a patient's limb, and its ends secured together so to encircle the limb in the manner of a ring.

As the thrust member is required to bear directly against the patient's body, it is preferably clad with cushioning material as indicated at 18.

In further preference, the tubular body portion 15 houses a strip 19 of stiff but flexible material, of plastics, steel or other material such that the thrust member is influenced to remain substantially straight and stiff to facilitate its application to a patient's limb from the side of the limb (that is, virtually at that part of the limb where the thrust member is required to be located, without having to lift the limb or negotiate the member along the full length of the limb) and yet be flexible enough to be easily brought to ring-form when required.

A pair of locator stubs 20 are mounted on the thrust member so that they protrude in the direction from which the mentioned caliper side members, or "legs", are to be applied to the thrust member during application of the splint. These stubs are preferably capable of slight displacement so as to facilitate application of the caliper legs thereto. The amount of this displaceability will be sufficient if the stubs project loosely through holes 21 in the body portion 15 and the cushioning material 18, as the end pieces of L-shaped shanks 22 housed in tube 15.

The U-shaped caliper consists of side members 23 and a crotch in the form of a plate 24 to which both members 23 are fixed, for example, by welding. Each member is in two telescopically adjustable parts 25 and 26 the latter (at least) being tubular. Selected length adjustment is held by chuck sleeves 27 which, by taper threads, thread on longitudinally-slit (28), threaded end pieces of parts 26.

The means to locate and retain location of the free ends of the side members 23 in relation to the thrust member, consists in the mentioned stubs 20 and the tubular free ends 29 of the side member parts 26. The ends 29, being tubular, can simply be ensleeved about the stubs, with the result as shown (at 30) in FIG. 9.

The caliper preferably has rectangularly down-bent ends 31 so that a support U-tube 32 can be applied, as a stand (as shown in FIG. 10) to ends 31 when the crotch end of the caliper is required to be elevated.

The tension means may be in the form of a sling comprising a main thong 33 and a branch thong 34. The free ends of these items are furnished with rings 35 which, when the sling is applied to a patient's limb, as shown in FIG. 9, can be brought together and attached by a tether 36 to a peg 37 on plate 24.

The tether could be in some form other than a chain as shown. For example it could be in the form of a strap having a row of holes for selected application to peg 37. If desired, the tether may include a spring balance so that the tension loading applied to a patient's limb may be read off.

The tether may be selectively attachable to the crotch plate 24 in some manner other than that described. For example, instead of having a peg such as 37 the plate 24 may have an upstanding lug or flange with a hole in it through which a threaded stem may be extended. This stem forms the end of the tether and variable tension is secured by use of a nut on the threaded stem.

In some cases it is necessary for a broken limb under traction by use of the splint hereof to be supported intermediately of its ends. For this purpose a number of bridge-pieces (one shown in FIG. 7) are provided. Each of these consists of a limb-support plate 38 having curled edge margins 39 suited to engage either of the parts 25 and 26 of the caliper side members as shown in FIG. 11.

It will be clear that these bridge-pieces may be easily applied to a caliper, from one side thereof, without substantial disturbance of the limb concerned. The bridge pieces are preferably made of metal, plastics or other relatively stiff material, so that they may be readily pushed under the limb and engaged with parts 25 or 26 without lifting the limb to any appreciable extent.

In use, as applied to a broken leg, the thrust member is slid under the patient's thigh close to the trunk of the body, and its ends joined so to encircle the thigh with the stubs 20 directed towards the patient's foot.

The caliper side members are adjusted for length, and the caliper is then placed in position by placing the tubular ends 29 (of parts 26) over the stubs 20. The sling is then applied to the patient's foot and the tether engaged with the peg 37, to give the required traction.

As previously indicated, the traction load may be measured by use of a spring balance, under most conditions however, traction may be gradually applied and ceased when the patient indicates relief from pain.

I claim:

1. A traction splint comprising:
(a) a thrust member sidewardly applicable to the proximal end of a patient's limb, and, adapted, when so applied, to bear against the patient's trunk at that proximal end, said thrust member comprising a strap furnished with means to join the strap ends together and having a tubular body portion, and a stiff but flexible means housed within said body portion which renders the thrust member substantially straight and stiff to facilitate its application to said patient's limb from the side and yet flexible enough to be easily brought to ring-form around the limb,
(b) a U-shaped caliper including length adjustable side members able to flank a broken limb longitudinally and on either side thereof, with the caliper crotch spaced from the distal end of the patient's limb,
(c) means to locate and retain location of the free ends of said side members in relation to said thrust member, and
(d) tension means able to take hold of the distal end of a patient's limb which has said caliper and said thrust member applied thereto as aforesaid, and adapted for attachment to said caliper crotch thereby to exert a degree of tension on the patient's limb.

2. A splint according to claim 1 wherein said strap is externally clad with cushioning material.

3. A splint according to claim 1 wherein said caliper consists of a pair of telescopically-adjustable, tubular side members and a bridge plate which constitutes a crotch portion for said side members;
said side members each being furnished with chuck means to hold selected adjustment of the member, and said bridge plate being furnished with means for selective attachment thereto of a tether secured to the patient's limb.

4. A splint according to any one of claims 1, 2 or 3 wherein said means to locate and retain location of said side members relative to said thrust member comprise tubular distal end portions on said side members, and location stubs on said thrust member able to enter said tubular end portions.

5. A splint according to claim 4 wherein said tension means comprise a sling attachable to the distal end of a broken limb, an upstanding peg on said bridge plate, and a tether to join said sling to said peg in selected adjustment.

6. The combination with a splint according to claim 3 of a stiff bridge-piece comprising a limb support plate and curled edge margins on said plate able to engage about said side members.

7. The combination with a splint according to claim 3, of down-bent portions on the crotch ends of said side-members, and a U-shaped support tube having tubular free ends able to accept said down-bent portions.

* * * * *